(12) United States Patent
Sasaki

(10) Patent No.: US 11,241,531 B2
(45) Date of Patent: Feb. 8, 2022

(54) MEDICAL LIQUID ADMINISTRATION DEVICE

(71) Applicant: TERUMO KABUSHIKI KAISHA, Tokyo (JP)

(72) Inventor: Shohei Sasaki, Chigasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 336 days.

(21) Appl. No.: 16/360,994

(22) Filed: Mar. 21, 2019

(65) Prior Publication Data

US 2019/0217007 A1 Jul. 18, 2019

Related U.S. Application Data

(63) Continuation of application No. PCT/JP2017/030604, filed on Aug. 25, 2017.

(30) Foreign Application Priority Data

Sep. 27, 2016 (JP) .............................. JP2016-188563

(51) Int. Cl.
*A61M 5/145* (2006.01)
*A61M 5/168* (2006.01)
(Continued)

(52) U.S. Cl.
CPC .......... *A61M 5/1456* (2013.01); *A61M 5/168* (2013.01); *A61M 5/16831* (2013.01);
(Continued)

(58) Field of Classification Search
CPC .. A61M 5/145; A61M 5/16831; A61M 5/172; A61M 5/16877;
(Continued)

(56) References Cited

U.S. PATENT DOCUMENTS

2003/0205587 A1 11/2003 Tribe et al.
2007/0088267 A1* 4/2007 Shekalim .......... A61M 5/16854
604/134
(Continued)

FOREIGN PATENT DOCUMENTS

CN 1662269 A 8/2005
CN 105517594 A 4/2016
(Continued)

OTHER PUBLICATIONS

Extended European Search Report dated Mar. 16, 2020 in corresponding European Patent Application No. 17855520.7.
(Continued)

*Primary Examiner* — Shefali D Patel
*Assistant Examiner* — Avery Smale
(74) *Attorney, Agent, or Firm* — Foley & Lardner LLP

(57) ABSTRACT

A medical liquid administration device includes a flowing portion including a flow path through which a medical liquid is to flow; a medical liquid storage communicating with the flowing portion, the medical liquid storage storing the medical liquid that is to be fed to the flowing portion; a drive mechanism comprising a motor configured to generate a driving force for feeding the medical liquid stored in the medical liquid storage to the flow path; a detection unit configured to detect whether an operating state of the drive mechanism is within a preset range; and a controller configured to determine a blockage in the flowing portion and a failure in the drive mechanism.

6 Claims, 8 Drawing Sheets

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 5/145* (2013.01); *A61M 5/16877* (2013.01); *A61M 2205/073* (2013.01); *A61M 2205/18* (2013.01); *A61M 2205/3306* (2013.01)

(58) Field of Classification Search
CPC .......... A61M 2005/16863; A61M 2205/3306; A61M 2205/18; A61M 2205/103; A61M 5/1456; A61M 5/1723; A61M 5/142; A61M 2205/073; A61M 5/1413; A61M 2005/14208; A61M 5/14248; A61M 2005/14252; A61M 2005/14268; A61M 5/14276; A61M 2005/14284; A61M 2005/14506; A61M 5/1452; A61M 2005/14533; A61M 2005/1585; A61M 2005/1586; A61M 2005/1588; A61M 5/168; A61M 5/16804; A61M 2005/16868; A61M 2005/16872; A61M 2205/04; A61M 2205/10; A61M 2205/106; A61M 2205/12; A61M 2205/121; A61M 2205/123; A61M 2205/50

See application file for complete search history.

(56) References Cited

U.S. PATENT DOCUMENTS

| | | |
|---|---|---|
| 2012/0078222 A1 | 3/2012 | Smith et al. |
| 2012/0192951 A1* | 8/2012 | Yodfat .............. A61M 5/16831 137/1 |
| 2015/0238689 A1 | 8/2015 | Shimizu |
| 2017/0296731 A1* | 10/2017 | Crawford ................ A61M 1/28 |

FOREIGN PATENT DOCUMENTS

| | | |
|---|---|---|
| JP | 2002-113099 A | 4/2002 |
| JP | 2002-136594 A | 5/2002 |
| JP | 2009-521998 A | 6/2009 |
| JP | 2013-537844 A | 10/2013 |

OTHER PUBLICATIONS

Office Action dated Nov. 19, 2020 in corresponding Chinese Patent Application No. 201780042704.7.
International Searching Authority, "International Search Report," issued in connection with International Patent Application No. PCT/JP2017/030604, dated Dec. 5, 2017.
International Searching Authority, "Written Opinion," issued in connection with International Patent Application No. PCT/JP2017/030604, dated Dec. 5, 2017.
Translation of the Written Opinion dated Dec. 5, 2017 in corresponding PCT application No. PCT/JP2017030604.

* cited by examiner

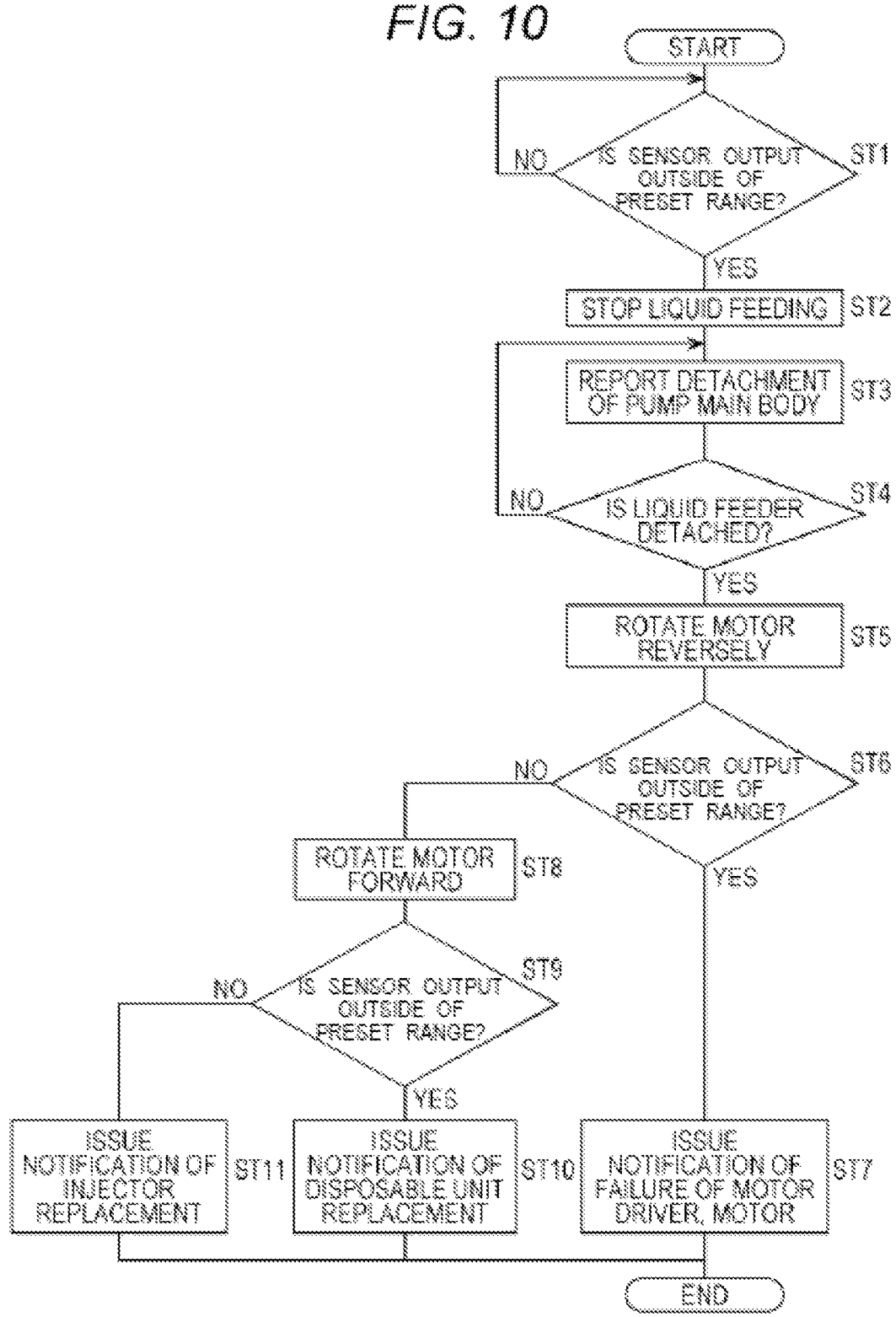

MEDICAL LIQUID ADMINISTRATION DEVICE

CROSS-REFERENCE TO RELATED APPLICATIONS

This is a bypass continuation of PCT Application No. PCT/JP2017/030604, filed on Aug. 25, 2017, which claims priority to Japanese Application No. 2016-188563, filed on Sep. 27, 2016. The contents of these applications are hereby incorporated by reference in their entireties.

BACKGROUND

The present disclosure relates to a medical liquid administration device to be used for administering a medical liquid into a living body.

Conventionally, as a device administrating a medical liquid such as insulin, there has been known a portable administration device that continuously administers a medical liquid with the administration device attached to the skin of a patient or subject to whom the medical liquid is administered.

In such a medical liquid administration device, although it is uncommon during normal use, an operation in case of an abnormality may be predetermined when unexpected circumstances arise. In the conventional technique relating to an operation in an abnormal state, the timer included in the control unit monitors the speed of the motor, and in a case in which the speed falls below a predetermined range, the control unit stops the actuator for causing the plunger that pushes out the medical liquid in the syringe to operate (e.g., refer to JP 2002-136594 A).

SUMMARY

In a case in which an abnormality occurs in the medical liquid administration device as described above, it is necessary to replace the entire device or to identify a component providing the cause of abnormality and to replace the component or a group of components that includes the component. In the case of replacing only the necessary component, in JP 2002-136594 A, the operations of the motor are monitored. However, it is difficult to identify whether the abnormality is due to failure of the motor or due to blockage of a flow path for the medical liquid to be administered through the flow path.

An object of certain embodiments described in the present disclosure is to provide a medical liquid administration device capable of discriminating between failure of a drive mechanism such as a motor and blockage of a flowing portion that forms a flow path.

According to one embodiment, a medical liquid administration device includes: a flowing portion including a flow path through which a medical liquid is to flow; a medical liquid storage communicating with the flowing portion, the medical liquid storage storing the medical liquid that is to be fed to the flowing portion; a drive mechanism including a motor configured to generate a driving force for feeding the medical liquid stored in the medical liquid storage to the flow path; a detection unit configured to detect whether an operating state of the drive mechanism within a preset range; and a controller configured to control the drive mechanism, the controller being configured to perform determination based on an output from the detection unit. The controller stops liquid feeding from the flowing portion in a case in which the output from the detection unit is outside the preset range, determines occurrence of blockage in the flowing portion when the output of the detection unit is within the preset range with the motor rotating in a reverse rotation direction to a rotation direction of the motor during the liquid feeding, and determines occurrence of failure in the drive mechanism when the output is outside the preset range.

According to the medical liquid administration device of certain embodiments, for occurrence of blockage in the flowing portion that forms the flow path, when the motor rotates in the reverse rotation direction to the liquid feeding, the output from the detection unit is within the preset range. On the other hand, for presence of abnormality in the drive mechanism, the output of the detection unit is outside the preset range even in the reverse rotation. Therefore, the arrangement as described above enables discrimination between the blockage in the flowing portion and the failure in the drive mechanism.

BRIEF DESCRIPTION OF THE DRAWINGS

FIG. 4(A) is a view illustrating a state before introduction of a cannula into a living body, and FIG. 4(B) is a view illustrating the cannula introduced into the living body with a puncturing tool. FIG. 4(C) is a view illustrating the cannula indwelled in the living body after the puncturing tool is removed.

FIG. 7(A) is a view illustrating a state before the injector and the liquid feeder are connected, and FIG. 7(B) is a view illustrating the injector and the liquid feeder connected.

FIG. 10 is a flowchart illustrating identification of a cause of failure in the medical liquid administration device according to a second embodiment.

DETAILED DESCRIPTION

Hereinafter, embodiments of the present invention will be described with reference to the accompanying drawings. Note that the following description does not limit the technical scope or the meaning of the terms described in the claims. In addition, the dimensional ratios of the drawings are exaggerated for convenience of description and may differ from the actual ratios.

First Embodiment

Hereinafter, with reference to FIGS. 1 to 9, a medical liquid administration device according to a first embodiment will be described in detail. FIGS. 1 to 8 are views for describing the configuration of each part of the medical liquid administration device according to the present embodiment.

The medical liquid administration device according to the present embodiment is provided as a portable insulin administration device 100 that feeds insulin as a medical liquid into the living body of a diabetic patient who is the user. In the following description, the medical liquid administration device will be described as the insulin administration device 100.

Figure 1:
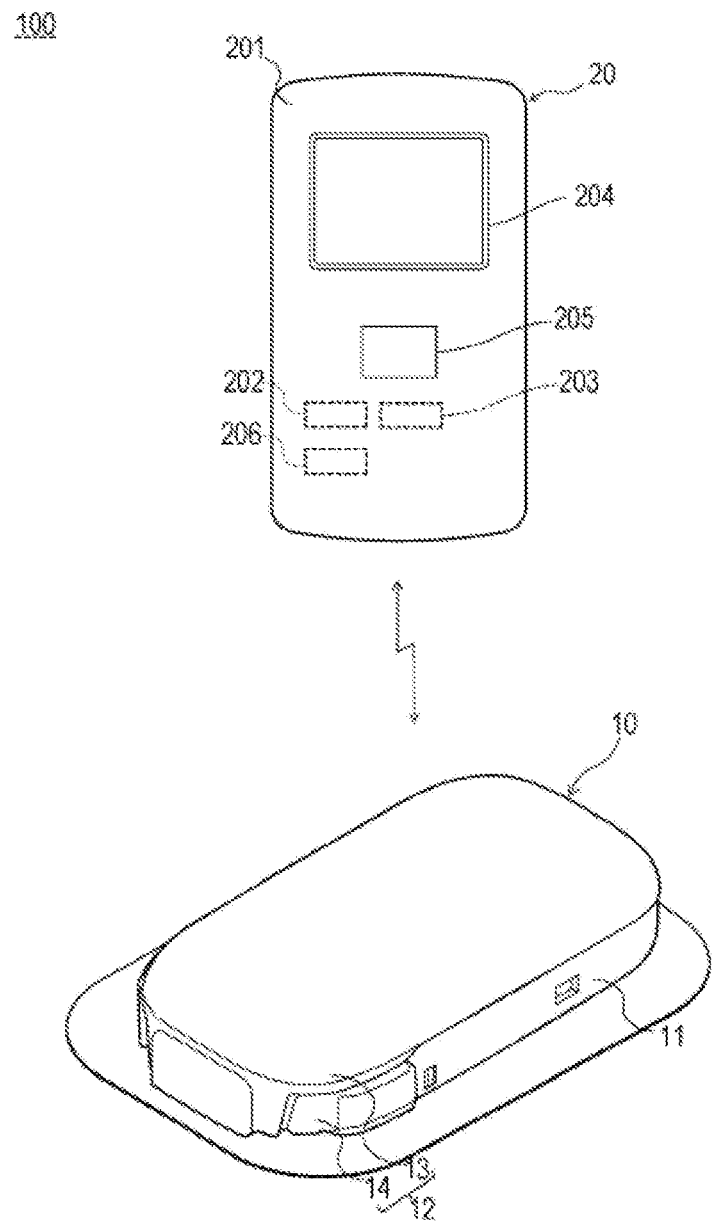
FIG. 1 is a schematic view illustrating a medical liquid administration device according to a first embodiment of the present invention.

As illustrated in FIG. 1, the insulin administration device 100 includes: a liquid-feeder main body 10 that performs a liquid feeding operation of feeding insulin as a medical liquid into the living body; and a remote controller 20 that performs various operation instructions to the liquid-feeder main body 10. Hereinafter, the configuration of each part of the insulin administration device 100 will be described in detail.

Figure 2:
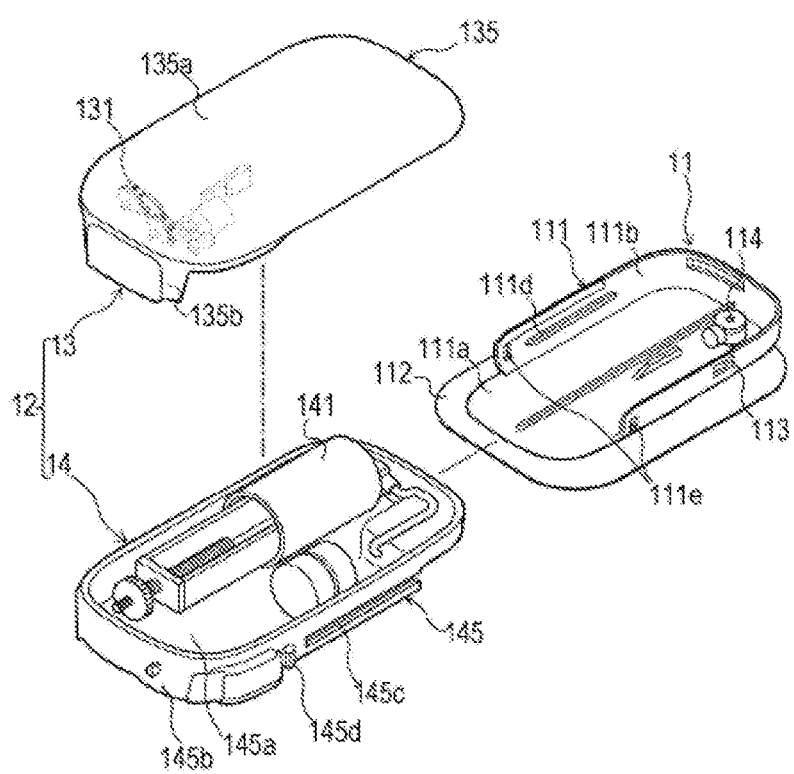
FIG. 2 is an exploded perspective view illustrating a liquid-feeder main body of the medical liquid administration device.
Figure 3:
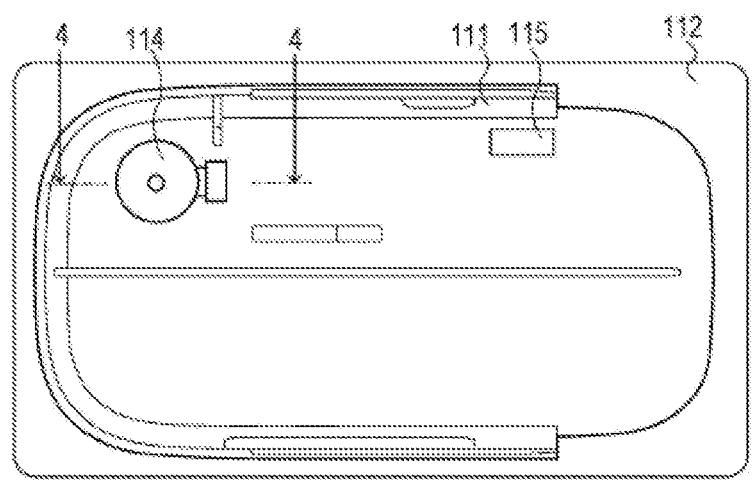
FIG. 3 is a plan view illustrating an injector of the medical liquid administration device.

As illustrated in FIG. 2, the liquid-feeder main body 10 includes: an injector 11 to be attached to the living body of the user, the injector 11 including a cannula 113 or the like to be indwelled in the living body of the user; and a liquid feeder 12 including a liquid-feeder reusable unit 13 and a liquid-feeder disposable unit 14. The liquid-feeder reusable unit 13 includes a drive mechanism 131 or the like that generates a driving force of causing a member necessary for a liquid feeding operation to drive. The liquid-feeder disposable unit 14 includes: a medical liquid storage 141 filled with insulin; and a pushing mechanism 143 or the like to be described later that is to be used for feeding the medical liquid filled in the medical liquid storage 141.

The injector 11 and the liquid feeder 12 are separably coupled. For example, when bathing or the like, while attaching the injector 11 to the living body, the user separates, from the injector 11, the liquid feeder 12 including the medical liquid storage 141 filled with insulin, and an electrical and mechanical mechanism. Performance of this separation enables prevention of warming of the insulin in the medical liquid storage 141 or wetting by the liquid adhered to the electrical and mechanical mechanism in the liquid feeder 12.

In addition, the liquid-feeder reusable unit 13 and the liquid-feeder disposable unit 14 are separably coupled. After a predetermined period of use, in a case in which the insulin or the like in the medical liquid storage 141 is used up, the liquid-feeder reusable unit 13 and the liquid-feeder disposable unit 14 are separated from each other, and the liquid-feeder disposable unit 14 can be throwaway (disposal) to replace with a new one. On the other hand, in liquid-feeder reusable unit 13, there is installed a constituent member such as a motor 136 or a gear group 137 that is less replaced or expensive than the constituent members installed in the liquid-feeder disposable unit 14. As described above, the constituent members to be discarded after the use for a predetermined period and the relatively expensive constituent members are installed in respective housings, and the relatively expensive constituent members are installed in the liquid-feeder reusable unit 13 for reuse. This arrangement enables reduction in manufacturing cost for the device or cost associated with use of the device. Each configuration will be described below.

First, the injector 11 will be described. As illustrated in FIG. 2 and the like, the injector 11 includes; an injector main body (also referred to as a cradle) 111; an adhesion portion 112 that is to adhere the injector main body 111 to the living body of the user; the cannula 113 protruding from the injector main body 111, the cannula 113 being to be indwelled in the living body; a support member 114 placed on the injector main body 111, the support member 114 supporting the cannula 113; and a magnet 115 (refer to FIG. 3) to be used for detecting the coupling between the injector 11 and the liquid feeder 12.

Figure 4A:
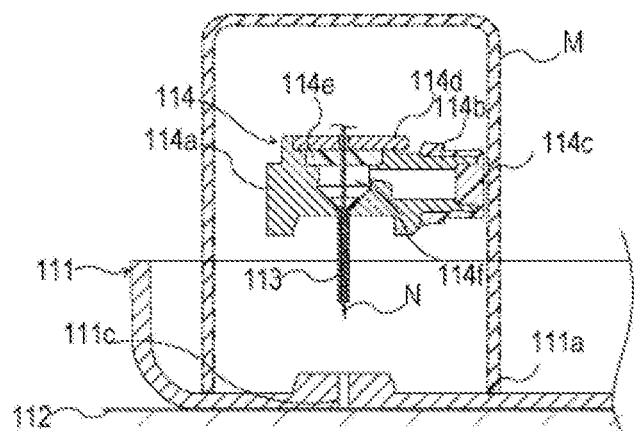
FIGS. 4(A) through 4(C) are enlarged cross-sectional views taken along line 4-4 of FIG. 3.
Figure 4B:
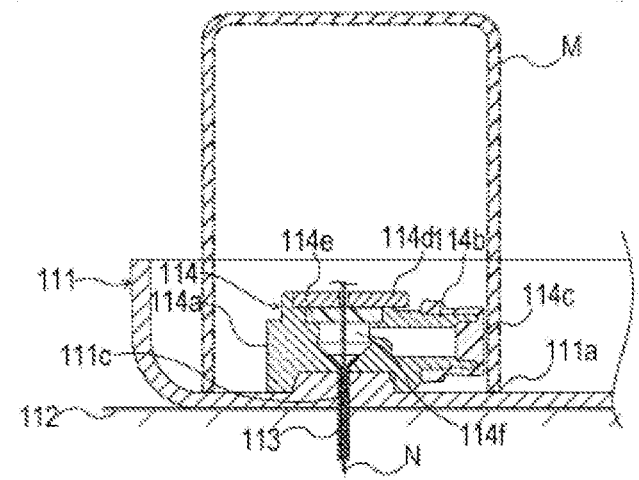
Figure 4C:
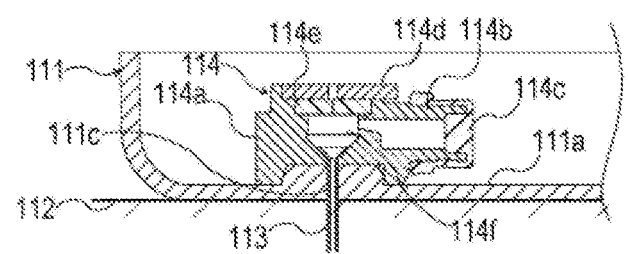

As illustrated in FIG. 2, the injector main body 111 includes: a flat plate-shaped placement portion 111a; and a longitudinal wall 111b formed by raising a portion of the outer peripheral edge of the placement portion 111a. As illustrated in FIGS. 4(A) to (C), an insertion hole 111c through which the cannula 113 can be inserted is formed at the placement portion 111a.

In addition, as illustrated in FIG. 2, at the longitudinal wall 111b, there is formed a protrusion 111d protruding toward an opposed face and a through hole 111e, as an engaging portion for maintaining the mechanical coupling with a second housing 145 of the liquid-feeder disposable unit 14 to be described later. When the second housing 145 of the liquid-feeder disposable unit 14 is slid to be coupled to the injector main body 111, the protrusion 111d fits into a groove 145c outside the second housing 145. In addition, a hooking portion 145d on the second housing 145 is hooked through the through hole 111e. Note that the shape of the engaging portion is not limited to the above-described shape as long as the injector main body 111 and the second housing 145 of the liquid-feeder disposable unit 14 are separably coupled.

As illustrated in FIG. 3 and FIGS. 4(A) to (C), the adhesion portion 112 includes a substantially rectangular sheet-shaped member. Adhesiveness is added to a face of the adhesion portion 112 on the side opposite to a face on the side where the longitudinal wall 111b rises in the placement portion 111a of the injector main body 111. The adhesion portion 112 is capable of adhering the injector 11 to the living body of the user with the adhesiveness of the adhesion portion 112 itself. Noted that the adhesion portion 112 may be prevented from inadvertently adhesion, by using a detachable release paper or the like that covers and protects the adhesion portion 112 on the face of the adhesion portion 112, the face having the adhesiveness to be adhered to the living body.

The cannula 113 is to be punctured into the living body and to be used in order to introduce a medical liquid such as insulin from the medical liquid storage 141 into the living body. As illustrated in FIG. 4(A), the cannula 113 has a cylindrical portion and a truncated conical portion continuously formed at the cylindrical portion, and an inner cavity for flowing insulin therethrough is continuously formed in the cylindrical portion and the truncated conical portion. Having the shape described above, the cannula 113 has a shape like a so-called funnel. Needless to say, the shape of the cannula 113 is not limited to the above-described shape as long as the cannula 113 is capable of introducing the medical liquid from the medical liquid storage 141 into the living body.

Figure 7A:
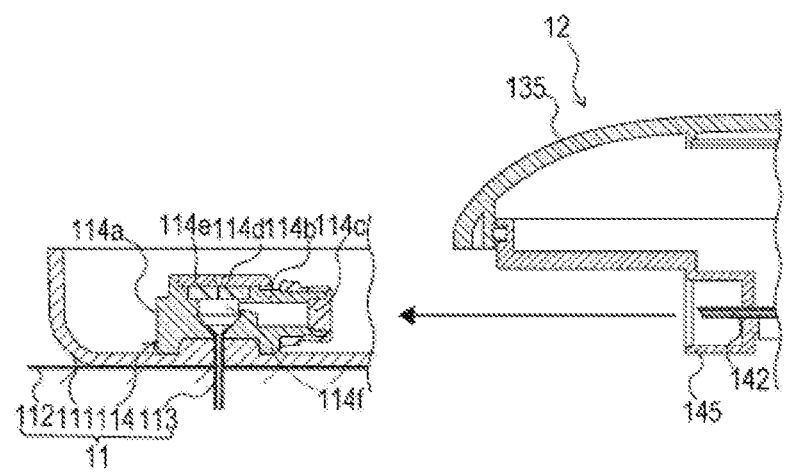
FIGS. 7(A) and 7(B) are cross-sectional views taken along line 7-7 of FIG. 5.
Figure 7B:
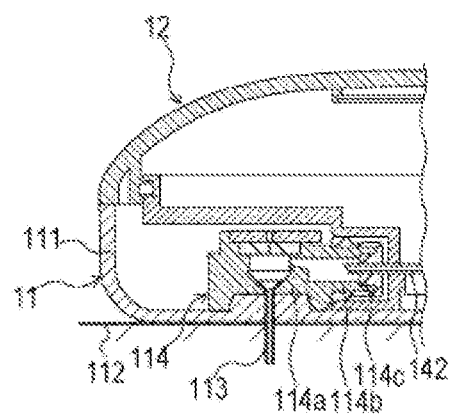

As illustrated in FIGS. 4(A) through 4(C), the support member 114 includes: a base portion 114a supporting the cannula 113; a connection port 114b including an inner cavity into which a liquid feed tube 142 (refer to FIGS. 7(A) and 7(B)) of the liquid-feeder disposable unit 14 is inserted; a cap 114c attached covering the connection port 114b; a lid member 114d attached to an upper face (face on the side opposite to a placing face on the injector main body 111) of the base portion 114a; and a sealing member 114e provided between the base portion 114a and the lid member 114d.

The base portion 114a is a portion includes the base of the support member 114, and in the present embodiment, the base portion 114a has a substantially cylindrical shape. As illustrated in FIG. 4(C) and the like, the base portion 114a has inner space 114f in which the cannula 113 is provided, and the inner space 114f has a funnel shape according to the shape of the cannula 113 so as to be able to support the cannula 113.

As illustrated in FIG. 4 (A) and the like, the connection port 114b extends in a direction intersecting a cylindrical shaft included in the cannula 113, in the base portion 114a. The inner cavity of the connection port 114b communicates with the inner space 114f of the base portion 114a.

The cap 114c is preferably formed of a material capable of inserting the liquid feed tube 142 of the liquid-feeder disposable unit 14 to be described later and keeping the liquid-tightness between the liquid feed tube 142 and the connection port 114b, and examples of such a material includes a rubber or the like.

As illustrated in FIG. 4(C), the lid member 114d has a function of pressing the sealing member 114e. In the lid member 114d, a through hole is formed coaxially with the axial direction of the cannula 113, through which a needle N of a puncturing tool M to be described later can be inserted.

The sealing member 114e is provided so as to be able to insert the needle N of the puncturing tool M and prevent insulin from leaking out from the through hole of the lid member 114d after the puncturing tool M is removed. Examples of the material of the sealing member 114e include rubber or the like. Note that the puncturing tool M illustrated in FIGS. 4(A) and (B) is illustrated with the detailed configuration omitted.

The cannula 113 in the living body can be indwelled, for example, with the puncturing tool M including the needle N insertable through the inner cavity of the cannula 113 supported by the support member 114, and a biasing member (not illustrated) that applies a biasing force to the support member 114 and the needle N in a direction where the needle N and the cannula 113 are to protrude from the placement portion 111a.

Specifically, first, the user attaches the injector main body 111 onto the user's own body surface with the adhesion portion 112. Next, the needle N is inserted from the through hole in the lid member 114d of the support member 114, and the support member 114 is attached to the puncturing tool M such that the needle N is inserted through the inner cavity of the cannula 113. Next, as illustrated in FIG. 4(A), the puncturing tool M is attached on the placement portion 111a. Next, as illustrated in FIG. 4(B), the support member 114 and the needle N are ejected toward the direction where the needle N and cannula 113 are to protrude from the placement portion 111a, with the urging force of the urging member provided with the puncturing tool M. At this time, the support member 114 is secured to the placement portion 111a with a latching mechanism (not illustrated). Next, as illustrated in FIG. 4(C), the puncturing tool M including the needle N is detached from the placement portion 111a with the support member 114 attached on the placement portion 111a. This allows the cannula 113 to be indwelled in the living body.

Note that, in this specification, the cannula 113 and the support member 114 correspond to a flowing portion provided with a flow path through which a medical liquid that is to flow, and correspond to a first flowing portion of the flowing portion.

The magnet 115 is to be used in order to detect that the liquid feeder 12 is coupled to the injector 11. As described later, the liquid-feeder disposable unit 14 included in the liquid feeder 12 is provided with a mounting detection unit 139 to be used together with the magnet 115 for detecting the coupling between the liquid feeder 12 and the injector 11 as described later. In the present embodiment, the mounting detection unit 139 includes a reed switch, and is provided in a first housing 135 of the liquid-feeder reusable unit 13 to be described later. The reed switch is disposed so as to locate above the head of the magnet 115 when the liquid feeder 12 is attached to the injector 11. The reed switch includes metal plates disposed spaced apart from each other inside a glass tube, and the metal plates come into contact with each other due to the disposition of the reed switch above head of the magnet 115 near the reed switch. The mounting detection unit 139 is electrically connected to a first controller 134 to be described later, so that the mounting detection unit 139 is capable of detecting whether or not the liquid feeder 12 is attached to the injector 11 through detection of contact or noncontact of the metal plates of the mounting detection unit 139.

Figure 5:
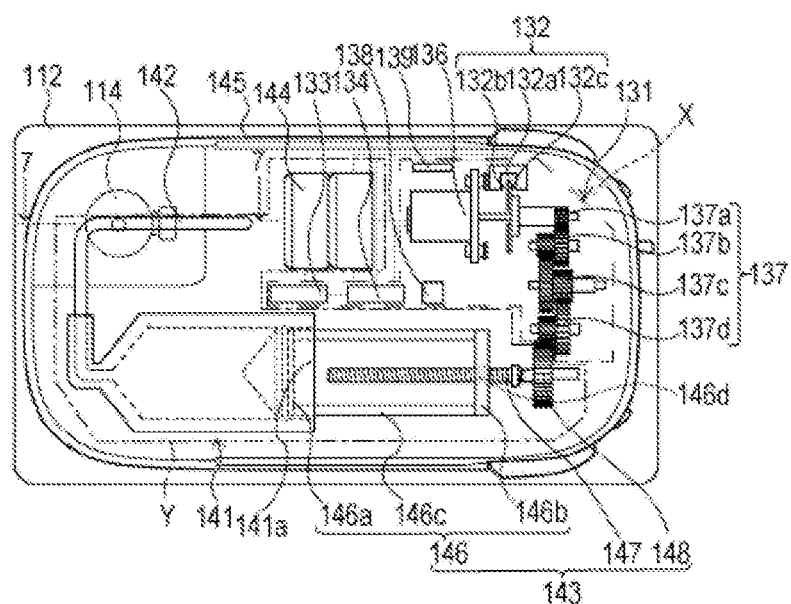
FIG. 5 is a schematic plan view illustrating the structure of each part in the liquid-feeder main body of the medical liquid administration device according to the first embodiment.

Next, the liquid-feeder reusable unit 13 will be described. As illustrated in FIGS. 2 and 5, the liquid-feeder reusable unit 13 includes: the drive mechanism 131 that drives a member necessary for performing a liquid feeding operation; a rotation detection unit 132 that detects a rotation operation of the drive mechanism 131; a first communication unit 133 that communicates with the remote controller 20; the first controller 134 that controls the drive mechanism 131, the first communication unit 133, or the like; a first housing 135 that retains these constituent elements; and the mounting detection unit 139 to be used when mounting of the liquid feeder 12 to the injector 11 is detected. Note that, in FIG. 5, a portion surrounded by a dotted line X represents components attached to the liquid-feeder reusable unit 13, and a portion surrounded by a one-dot chain line Y represents components attached to the liquid-feeder disposable unit 14. In addition, FIG. 5 is illustrated with the first housing 135 omitted in order to facilitate understanding.

As illustrated in FIG. 5 and the like, the drive mechanism 131 includes: the motor 136 provided with an output shaft that causes rotation with electric power from a battery 144 of the liquid-feeder disposable unit 14; the gear group 137 that decelerates the rotation caused by the motor 136 to transmit the rotation to the pushing mechanism 143 of the liquid-feeder disposable unit 14; and a motor driver 138 that controls the operations of the motor 136.

The motor 136 causes, on the output shaft, a driving force necessary for moving a sliding portion 146 of the pushing mechanism 143, as a rotational motion. As the motor 136, a stepping motor is used in the present embodiment. The stepping motor is preferable from the viewpoint of safety and the like because the rotation of the motor stops at short circuit. However, the specific aspect of the motor 136 is not limited to such a stepping motor as long as the motor 136 is capable of generating a driving force due to rotation and has a size installable in the portable insulin administration device 100. In addition to the stepping motor, the motor 136 may be, for example, a direct current (DC) motor, an alternate current (AC) motor, or the like.

The motor driver 138 is electrically connected to the first controller 134 to be described later, and controls operations such as forward rotation, reverse rotation, and stop of the motor 136.

The gear group 137 is to be used in order to transmit the rotational power caused by the motor 136 to the pushing mechanism 143 that is to press the medical liquid storage 141. In the present embodiment, as illustrated in FIG. 5, the gear group 137 includes: a first gear 137a connected to a motor 136; a second gear 137b; a third gear 137c; and a fourth gear 137d, in which the second gear 137b, the third gear 137c, and the fourth gear 137d each mesh with adjacent gears.

The first gear 137a is provided with one type of teeth meshing with the adjacent gear. On the other hand, the second gear 137b, the third gear 137c, and the fourth gear 137d each are provided with two types of teeth meshing with the adjacent gears, the two types of teeth being in series in the direction of a shaft around which the gear rotates.

The second gear 137b is disposed adjacent to the first gear 137a and the third gear 137c in a direction (vertical direction in FIG. 5) intersecting the rotary shaft of the first gear 137a.

The third gear 137c is disposed adjacent to the second gear 137b and the fourth gear 137d in the direction (vertical direction in FIG. 5) intersecting the rotary shaft of the first gear 137a.

The fourth gear 137d is disposed adjacent to the third gear 137c and a fifth gear 148 of the liquid-feeder disposable unit 14 in the direction (vertical direction in FIG. 5) intersecting the rotary shaft of the first gear 137a.

The gear group 137 and the fifth gear 148 each include a spur gear. However, the gear group 137 and the fifth gear 148 are not limited to such a spur gear as long as the gear group 137 and the fifth gear 148 are capable of transmitting the power due to the rotation from the motor 136 to the pushing mechanism 143. In addition, for the gear group 137 and the fifth gear 148, the number of gears, the number of teeth, and the like are set such that the gear group 137 and the fifth gear 148 decelerate torque from the motor 136 to a set value. However, the specifications such as the number of gears and the number of teeth are not limited to the above numbers as long as a desired reduction gear ratio can be obtained within given space. Furthermore, in the present embodiment, a rotation direction of the gear on the input side corresponding to the first gear 137a and a rotation direction of the gear on the output side corresponding to the fifth gear 148 may be identical to or different from each other. The material of the gear group 137 is not particularly limited as long as an output from an output shaft 136a of the motor 136 can be transmitted to the pushing mechanism 143, and examples of the material include a metal, or a resin material such as plastic.

In addition, the motor 136 is connected to the first gear 137a of the gear group 137 via a coil spring (not illustrated).

As illustrated in FIG. 5, the rotation detection unit 132 includes; an intercepting member 132a disposed on the motor 136 side of the first gear 137a; and an optical sensor including a light emitting unit 132b and a light receiving unit 132c disposed opposed to each other with the intercepting member 132a interposed therebetween.

Figure 6:
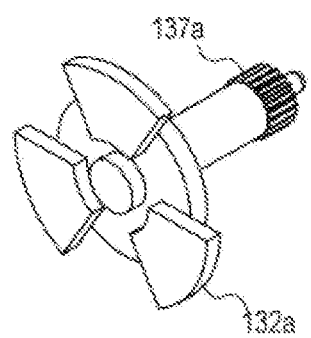
FIG. 6 is a perspective view illustrating an intercepting member included in a rotation detection unit that detects rotation of a motor included in a drive mechanism.

As illustrated in FIG. 6, the intercepting member 132a is provided with a plurality of substantially fan-like shapes such as blades of an electric fan at constant angular intervals in the circumferential direction of the first gear 137a. When detection light emitted from the light emitting unit 132b of the optical sensor passes through a portion where the blade shapes of the intercepting member 132a are not provided, the light receiving unit 132c receives the detection light S. On the contrary, when the detection light S from the light emitting unit 132b is intercepted by the blade shapes of the intercepting member 132a, the light receiving unit 132c does not receive the detection light S. The blade shapes of the intercepting member 132a are provided at the constant intervals, whereby the rotational speed of the output shaft of the motor 136 is detected based on a time interval (frequency) at which the detection light S is received. The respective speed reduction ratios of the gear group 137 and the fifth gear 148, and the screw pitch of a feed screw 147 of the pushing mechanism 143 are fixed (invariable). Thus, the amount of liquid feeding of the medical liquid can be detected through the detection of the rotational speed of the output shaft 136a of the motor 136. A preset range to be detected by the rotation detection unit 132 may be, for example, a rotational speed of the motor 136 in a range of 60 to 300 rpm.

Note that although the intercepting member 132a is provided with three pieces of fan-like blade shapes in FIG. 6 and the like, the blade shape and the number of blade shapes are not limited to those in FIG. 6 as long as intercepting and passing of the detection light S can be switched. Furthermore, in the present embodiment, the rotation detection unit 132 detects the rotational speed of the output shaft of the motor 136 to obtain the amount of liquid feeding. However, the method of detecting the amount of liquid feeding is not limited to the above-described method. For example, the amount of liquid feeding can also be obtained from a control signal sent to the motor 136. In addition, although the rotational speed is detected with the optical sensor; however, it is not limited to the optical sensor as long as the amount of rotation of the motor can be detected, and a magnetic sensor or the like may also be used in addition to the above.

The first communication unit 133 includes an electronic device necessary for communication with the remote controller 20. As described later, the remote controller 20 is provided with a second communication unit 202 such that the second communication unit 202 uses Bluetooth (registered trademark) low energy (BLE) communication as near field communication to be able to mutually transmit and receive information with the first communication unit 133 of the liquid-feeder reusable unit 13.

Figure 8:
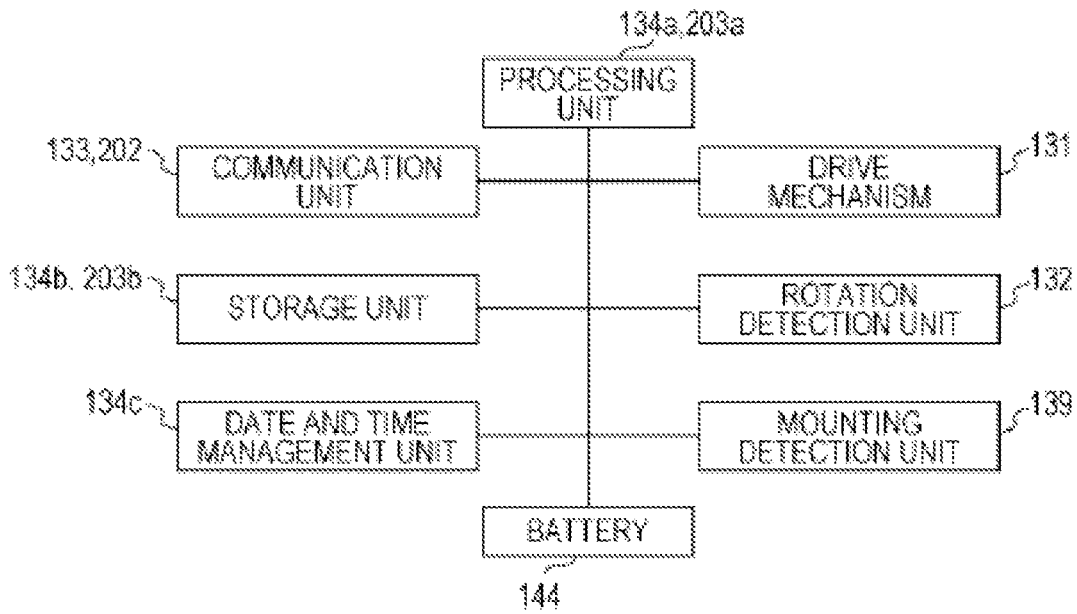
FIG. 8 is a block diagram illustrating the configuration of a control system of the medical liquid administration device.

As illustrated in FIG. 8, the first controller 134 includes a processing unit 134a, a storage unit 134b, and a date and time management unit 134c. The first controller 134 includes a known microcomputer, and controls the entire components that operate in the liquid feeder 12.

The processing unit 134a executes computations and commands necessary for the operations of the motor 136 included in the drive mechanism 131, the first communication unit 133, the rotation detection unit 132, and the like. The processing unit 134a includes a central processing unit (CPU) and the like.

The storage unit 134b stores an output of the rotational speed of the motor 136 from the rotation detection unit 132 and stores information on, for example, whether or not the liquid feeder 12 has been detached from the injector 11. The storage unit 134b includes a random access memory (RAM), a read-only memory (ROM), and the like.

The date and time management unit 134c is to be used when time information is necessary, for example, when the rotational speed of the motor 136, or the like is detected. The date and time management unit 134c includes a real time clock and the like.

As illustrated in FIG. 2, the first housing 135 has: an upper face 135a covering the constituent members such as the drive mechanism 131, the rotation detection unit 132, the first communication unit 133, the first controller 134, and the like; and a sidewall 135b formed by raising a portion of the outer peripheral edge of the upper face 135a. The drive mechanism 131, the rotation detection unit 132, the first communication unit 133, the first controller 134, and the like each are operatively attached on the upper face 135a.

In addition, the first housing 135 has a protrusion (not illustrated) protruding inward from the inner face of the sidewall 135b, the protrusion allowing the liquid-feeder reusable unit 13 to be separably coupled to and separate from the liquid-feeder disposable unit 14. In the present embodiment, the first housing 135 includes a resin component such as plastic; however, the material is not limited to such plastic as long as the material has a certain degree of strength and the like. The mounting detection unit 139 has been described above, and the detailed description thereof will be omitted here. Note that the mounting detection unit 139 corresponds to a connection detection unit that detects connection between the liquid feed tube 142 included in the liquid feeder 12 and the cannula 113 and the support member 114 included in the injector 11.

Next, the liquid-feeder disposable unit 14 will be described. As illustrated in FIG. 5, the liquid-feeder disposable unit 14 includes: the medical liquid storage 141 filled with insulin; the liquid feed tube 142 communicating with the inner cavity of the connection port 114b provided in the injector 11 and the medical liquid storage 141; the pushing mechanism 143 mechanically connected to the drive mechanism 131, the pushing mechanism 143 that is to push the insulin in the medical liquid storage 141 to the liquid feed tube 142; the battery 144 that supplies electric power to the drive mechanism 131 and the like; and the second housing 145 that retains these constituent elements.

The medical liquid storage 141 has a tubular shape. The liquid feed tube 142 is connected to one end of the medical liquid storage 141. An opening 141a is formed at the other end of the medical liquid storage 141. The sliding portion 146 of the pushing mechanism 143 to be described later is inserted from the opening 141a into the medical liquid storage 141, and the insulin is stored in space partitioned by the medical liquid storage 141 and the sliding portion 146.

As illustrated in FIGS. 7(A) and (B), in the present embodiment, the liquid feed tube 142 includes a thin metal tube having a sharp tip shape. As illustrated in FIG. 7(A), when the liquid feeder 12 is coupled to the injector 11 while being slid and moved, as illustrated in FIG. 7(B), the sharp tip of the liquid feed tube 142 passes through the cap 114c of the injector 11 to be inserted into the inner cavity of the connection port 114b. Note that, in the present embodiment, the liquid feed tube 142 corresponds to the flowing portion including the flow path through which the medical liquid is to flow from the medical liquid storage 141, and corresponds to a second flowing portion of the flowing portion, the second flowing portion being separably connected to the cannula 113 and the support member 114 included in the injector 11.

As illustrated in FIG. 5, the pushing mechanism 143 includes; the sliding portion 146 movable forward and backward in the inner space of the medical liquid storage 141; the feed screw 147 meshing with a female screw 146d at the sliding portion 146 to cause the sliding portion 146 to move backward and forward; and the fifth gear 148 meshing with the fourth gear 137d of the drive mechanism 131, the fifth gear 148 connected to the feed screw 147.

As illustrated in FIG. 5, the sliding portion 146 includes: a pushing member 146a movable forward and backward in the medical liquid storage 141 while maintaining sealing such that the medical liquid does not leak out on the sliding portion 146 side; a feed plate 146b including the female screw 146d meshing with the feed screw 147; and a coupling plate 146c coupling the pushing member 146a and feed plate 146b.

The pushing member 146a is inserted from the opening 141a of the medical liquid storage 141 in order to form a space for containing the medical liquid in the inner space of the medical liquid storage 141. The pushing member 146a moves forward and backward in the left-right direction of the FIG. 5 while fitting onto a tubular inner wall face such that the medical liquid does not leak from the boundary between the pushing member 146a and the tubular inner wall face of the medical liquid storage 141. The size (volume) of the containing space (inner space of the medical liquid storage 141) for containing the medical liquid varies depending on the location of the pushing member 146a in the medical liquid storage 141. The pushing member 146a is also called a plunger, a pusher, or the like.

The feed plate 146b has a plate shape with a hole, the female screw 146d meshing with a male screw 147a of the feed screw 147 is provided through the hole.

The coupling plate 146c includes two plates coupling the pushing member 146a and the feed plate 146b. However, the shape of the coupling plate 146c is not limited to such a shape as long as the coupling plate 146c can couple the pushing member 146a and the feed plate 146b and the pushing member 146a and the feed plate 146b can integrally operate with each other. In addition to the above shape, the coupling plate 146c may have, for example, a hollow shape fitting onto the tubular inner wall face of the medical liquid storage 141 in the entire circumference of the tubular inner wall face.

The feed screw 147 has a general male screw shape, and a portion of the feed screw 147 meshes with the female screw 146d of the feed plate 146b. For example, a cruciform slot is provided on the head of the feed screw 147 and meshes with a portion of the fifth gear 148 to be described later.

The fifth gear 148 is disposed at a position where the fifth gear 148 meshes with the fourth gear 137d in the second housing 145, with the liquid-feeder reusable unit 13 and the liquid-feeder disposable unit 14 coupled to each other.

As illustrated in FIG. 5, the fifth gear 148 has gear teeth and a bit provided at an end of the rotary shaft that is the rotation center of the gear, the bit meshing (engaging) with the slot of the screw head of the feed screw 147.

The bit of the fifth gear 148 has a tip shape similar to that of a driver (also called a screwdriver, a wrench, or the like) that tightens a general screw. With the above-described arrangement, the bit of the fifth gear 148 meshes with the recessed slot of the screw head of the feed screw 147 to transmit power due to rotation of the fifth gear 148.

The teeth and the rotary shaft of the fifth gear 148 each have a shape similar to a known shape, and the description will be omitted.

The feed screw 147 and the fifth gear 148 are rotatably attached to the second housing 145.

When the fifth gear 148 rotates as the fourth gear 137d included in the drive mechanism 131 rotates, the feed screw 147 rotates. The feed plate 146b is restricted from rotating in a rotation direction of the feed screw 147, and the feed plate 146b moves along the spiral shaped shaft of the male screw of the feed screw 147 as the feed screw 147 rotates. The pushing member 146a coupled to the feed plate 146b via the coupling plate 146c moves in the medical liquid storage 141 as the feed plate 146b moves. When the pushing member 146a moves in a direction where the pushing member 146a is to be pushed into the medical liquid storage 141 (direction where the volume of the containing space decreases), the insulin in the containing space formed by the medical liquid storage 141 and the pushing member 146a is fed into the liquid feed tube 142. Note that even for occurrence of blockage in the liquid feed tube 142 or the cannula 113, the coupling plate 146c deflects by a predetermined amount, so that the motor 136 is rotatable a predetermined number of times.

When the liquid-feeder reusable unit 13 and the liquid-feeder disposable unit 14 are coupled, the battery 144 is electrically connected to the motor 136, the rotation detection unit 132, the first communication unit 133, the first controller 134, and the motor driver 138 in the liquid-feeder reusable unit 13 to supply electric power to the respective parts. In the present embodiment, the battery 144 includes two battery cells connected in series. However, the number of battery cells, the connecting method such as serial or parallel is not particularly limited as long as electric power can be supplied to each part.

As illustrated in FIG. 2, the second housing 145 has: a bottom face 145a at which the medical liquid storage 141, the liquid feed tube 142, the pushing mechanism 143, the battery 144 and the like are placed; and a sidewall 145b formed by raising the outer peripheral edge of the bottom face 145a.

The second housing 145 is separably coupled to the injector main body 111. Specifically, in the present embodiment, as illustrated in FIG. 2, the sidewall 145b is provided with a groove 145c fittable to the protrusion 111d at the injector main body 111, and the hooking portion 145d hooked through the through hole 111e in the injector main body 111. When the second housing 145 is slid and moved into the injector main body 111, the protrusion 111d of the injector main body 111 fits into the groove 145c of the second housing 145, and the hooking portion 145d of the second housing 145 is hooked through the through hole 111e of the injector main body 111. As a result, the second housing 145 is coupled to the injector main body 111.

In addition, the second housing 145 has a recess (not illustrated) meshing with the protrusion provided on the sidewall 135b of the first housing 135, so that the second housing 145 is separably coupled to the first housing 135. Coupling of the first housing 135 and the second housing 145 allows the drive mechanism 131 installed in the first housing 135 and the pushing mechanism 143 installed in the second housing 145 to be mechanically connected to each other. In addition, the motor 136, the rotation detection unit 132, the first communication unit 133, the first controller 134, and the motor driver 138 installed in the first housing 135 are electrically connected to the battery 144 installed in the second housing 145.

In the present embodiment, the second housing 145 includes a resin component such as plastic; however, the material is not limited to such plastic as long as the material has a certain degree of strength and the like similar to that of the first housing 135.

Next, the remote controller 20 will be described. As illustrated in FIG. 1, the remote controller 20 includes: a remote controller main body 201, the second communication unit 202 capable of wireless communication with the first communication unit 133; a second controller 203 that overall controls the insulin administration device 100; a monitor 204 (corresponding to a reporting unit) provided on the remote controller main body 201; a button 205 capable of accepting instruction contents from the user; and a battery 206 that supplies electric power to each part of the remote controller 20.

The remote controller main body 201 has a size large enough to be held with one hand by the user, and includes a relatively light resin component such as plastic.

The second communication unit 202 includes an electronic device necessary for communication with the first communication unit 133 of the liquid-feeder main body 10. In the present embodiment, the second communication unit 202 is provided so as to use Bluetooth (registered trademark) low energy (BLE) communication as a near field communication technology that enables communication with low power to be able to mutually transmit and receive information with the liquid-feeder main body 10. However, the communication method is not limited to BLE as long as wireless communication can be performed with the liquid-feeder main body 10.

As illustrated in FIG. 8, the second controller 203 includes a processing unit 203a and a storage unit 203b. The second controller 203 includes a known microcomputer, and controls the entire components that operate in the remote controller 20. The processing unit 203a executes computations and commands necessary for operations of the second communication unit 202, the monitor 204, and the like. The processing unit 203a includes a CPU and the like.

The storage unit 203b stores a program and the like necessary for controlling the second communication unit 202 and the monitor 204. The storage unit 203b includes a RAM, a ROM, or the like. For example, in a case in which the storage unit 203b includes the RAM and the ROM, the processing unit 203a reads each of various programs stored in the ROM in advance into the RAM and executes the programs, thereby causing operations such as a liquid feeding operation to be performed. Note that the monitor 204, the button 205, and the battery 206 have configurations similar to known ones, and the illustration and description in FIG. 8 are omitted.

Next, a usage example of the insulin administration device 100 will be described.

First, prior to use of the insulin administration device 100, the user mounts the injector 11 onto the living body, and performs a procedure of indwelling the cannula 113 in the living body with the puncturing tool M, as described above.

In addition, prior to use of the insulin administration device 100, the user couples and integrates the liquid-feeder reusable unit 13 and the liquid-feeder disposable unit 14 to form the liquid feeder 12. Then, the user operates the remote controller 20 and instructs priming (first priming) for filling insulin in the liquid feed tube 142 of the liquid-feeder disposable unit 14. Upon receipt of the instruction from the remote controller 20, the first controller 134 causes the drive mechanism 131 to operate moving the sliding portion 146 of the pushing mechanism 143 by a predetermined amount. As a result, the insulin contained in the medical liquid storage 141 is fed into the liquid feed tube 142, and the liquid feed tube 142 is filled with the insulin.

Next, the liquid feeder 12 is coupled to the injector 11.

Next, the user operates the remote controller 20 and instructs priming (second priming) such that the inner cavity of the cannula 113 is filled with the insulin.

Next, the user operates the remote controller 20 to appropriately select a liquid feeding mode such as a basal mode in which the insulin is continuously fed at a constant amount, and a bolus mode in which the amount of insulin feeding per unit time is increased temporarily, and then the insulin is fed into the living body.

Figure 9:
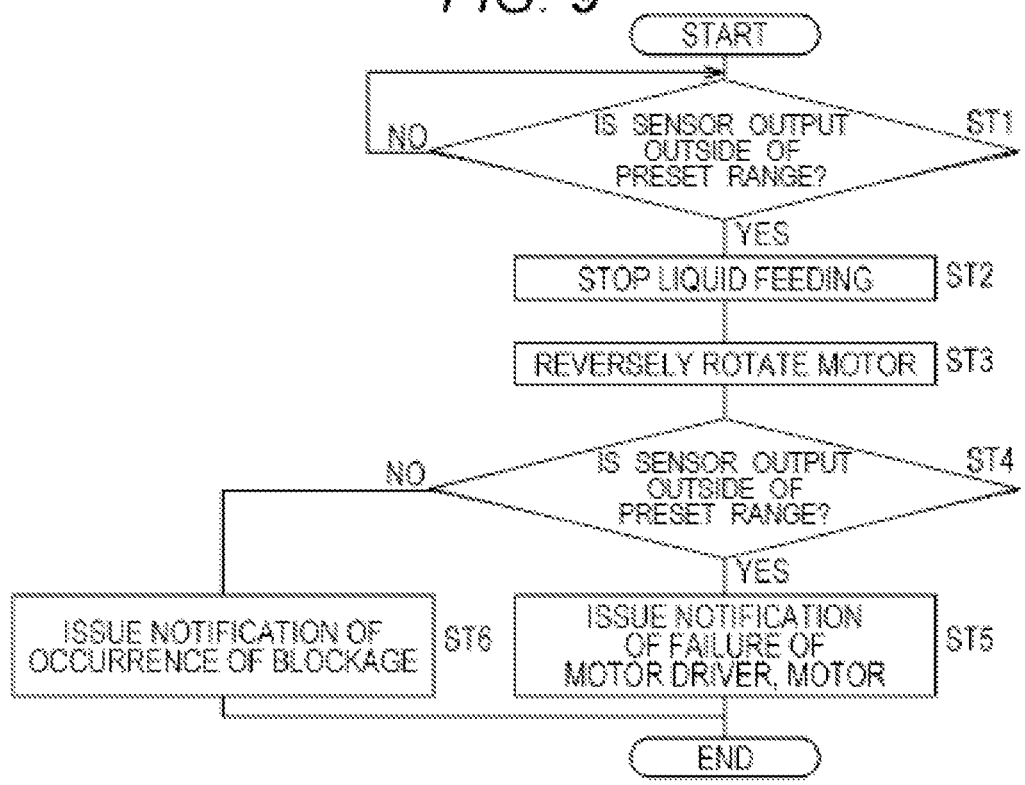
FIG. 9 is a flowchart illustrating identification of a cause of failure in the medical liquid administration device according to the first embodiment.

Next, an operation in a case in which an abnormality is found in the insulin administration device 100 will be described. FIG. 9 is a flowchart illustrating identification of a cause of failure in the insulin administration device according to the first embodiment of the present invention. In the following description, it is assumed that failure has occurred.

The rotation detection unit 132 having a sensing function discriminates whether an output that has been detected is in a preset range (ST1). In a case in which the output of the rotation detection unit 132 is within the preset range (ST1: NO), the subsequent operations are not performed.

In a case in which the motor 136 hardly rotates due to some circumstances, the output value may be below the preset range. In a case in which the output of the rotation detection unit 132 is outside the preset range (ST1: YES), the first controller 134 sends a signal to the drive mechanism 131 to stop liquid feeding by the operation of the drive mechanism 131 (ST2).

Next, the first controller 134 causes the drive mechanism 131 to operate in a reverse rotation direction to the case of feeding the insulin in the medical liquid storage 141 into to the liquid feed tube 142 with the pushing mechanism 143 (ST3). Then, the rotation detection unit 132 discriminates whether or not an output value of the rotation detection unit 132 is outside the preset range in the reverse rotation direction of the drive mechanism 131 to the case of feeding insulin (ST4).

If an abnormality is present in the motor driver 138 or the motor 136, the drive mechanism 131 is difficult to sufficiently operate regardless of either forward rotation or reverse rotation, so that the output of the rotation detection unit 132 indicates a value outside the preset range. Thus, in a case in which the output of the rotation detection unit 132 is outside the preset range (ST4: YES), the first controller 134 issues notification that the cause of failure is in the motor driver 138, the motor 136, or the like (ST5). In the present embodiment, the failure is displayed on the monitor 204 of the remote controller 20 and reported to the user.

On the contrary, in a case in which the output of the rotation detection unit 132 is within the preset range (ST4: NO), if the motor 136 reversely rotates to that during liquid feeding, the drive mechanism 131 and the pushing mechanism 143 operate normally. In this case, the motor 136 can reversely rotate due to elimination of deflection of the coupling plate 146c. From this result, it is conceivable that no failure occurs in the drive mechanism 131 such as the motor 136, and the cause of failure is present in another component forming the flow path, such as the liquid feed tube 142 or the cannula 113. In the above-described case, the first controller 134 instructs the monitor 204 to display notification indicating occurrence of blockage (ST6).

Next, the operation and effect of the present embodiment will be described. The insulin administration device 100 according to the present embodiment stops liquid feeding from the liquid feed tube 142 in a case in which the output detected by the rotation detection unit 132 is outside the preset range. In addition, based on the output of the rotation detection unit 132 during the rotation of the motor 136 in the reverse rotation direction to that during liquid feeding, it is identified whether the cause of failure is in the driving system component such as the motor 136 or blockage of the liquid feed tube 142 or the cannula 113 and the support member 114 or the like. As described above, in a case in which the cause of failure is in the driving system component such as the motor 136 or the like, the motor 136 or the like is difficult to rotate normally even if the motor 136 reversely rotates. On the other hand, for presence of abnormality in the liquid feed tube 142 or the like, the drive mechanism 131 can operate normally if the rotation is the reverse rotation. Thus, the arrangement as described above enables identification on whether failure is present in the driving system component or the liquid feed tube 142 or the like is blocked.

In addition, the insulin administration device 100 is capable of displaying the failure of the drive mechanism 131 or the like or the blockage of the liquid feed tube 142 or the like on the monitor 204 to urge the user to replace the component or the like.

Second Embodiment

FIG. 10 is a flowchart for describing a case of identifying a cause of failure in the insulin administration device according to a second embodiment of the present invention. In the first embodiment, in the case in which the output of the rotation detection unit 132 with the motor 136 rotating reversely is not outside the preset range, the occurrence of blockage is displayed on the monitor 204; however, the cause of failure can also be identified as follows. Note that, in the second embodiment, only the flow of determination in the case of identifying the failure differs, and the configuration of the components and the like included in the insulin administration device is the same as in the first embodiment; thus, the description will be omitted.

First, similarly to the first embodiment, the rotation detection unit 132 discriminates whether or not an output of the rotation detection unit 132 is outside the preset range (ST1). In a case in which the output is outside the preset range (ST1: YES), the first controller 134 sends a signal to the drive mechanism 131, so that liquid feeding due to the rotational operation of the drive mechanism 131 stops (ST2). Next, the first controller 134 causes the monitor 204 to display that the liquid feeder 12 including the liquid-feeder reusable unit 13 and the liquid-feeder disposable unit 14 is detached from the injector 11 (ST3).

Next, the first controller 134 refers to the storage unit 134b and verifies whether or not the liquid feeder 12 is detached from the injector 11 (ST4). In a case in which the liquid feeder 12 is not detached from the injector 11 (ST4: NO), the monitor 204 maintains the display of the report of the detachment. In addition, in order to urge the user to detach the liquid feeder 12, in addition to the above, while referring to the information from the date and time management unit 134c, if the liquid feeder 12 has still not been detached after elapse of a predetermined period of time from an initial report, an alarm or the like may be used to urge the user to detach the liquid feeder 12.

In a case in which the liquid feeder 12 is detached from the injector 11 (ST4: YES), the first controller 134 sends a signal to the drive mechanism 131 to rotate the motor 136 in the reverse direction to that during liquid feeding (ST5). Then, the first controller 134 discriminates whether an output of the rotation detection unit 132 is outside the preset range (ST6). In a case in which the output is outside the preset range (ST6: YES), the first controller 134 determines that an abnormality is present in the driving system component such as the motor 136, and displays the presence of abnormality, on the monitor 204 to report the abnormality to the user (ST7).

Conversely, in a case in which the output of the rotation detection unit 132 is within the preset range due to elimination of deflection of the coupling plate 146c (ST6: NO), the first controller 134 temporarily stops the operation of the drive mechanism 131, and then causes the drive mechanism 131 to operate in a rotation direction similar to that during the liquid feeding (ST8). Then, the first controller 134 verifies whether an output of the rotation detection unit 132 is outside the preset range in this state (ST9). Note that the preset range of the output of the rotation detection unit 132 in a rotation direction identical to that during the liquid feeding may be different from or identical to the preset range of the output of the rotation detection unit 132 in the reverse rotation direction to that during the liquid feeding.

In a case in which the output is outside the preset range (ST9: YES), the liquid feeder 12 is already detached from the injector 11. Thus, it is conceivable that no abnormality is present in the injector 11 and blockage has occurred in the liquid feed tube 142 included in the liquid feeder 12 forming the flow path. In this case, the first controller 134 determines occurrence of failure in the liquid-feeder disposable unit 14 including the liquid feed tube 142, and displays replacement of the liquid-feeder disposable unit 14, on the monitor 204 to report to the user (ST10).

Conversely, in a case in which the sensor output of the rotation detection unit 132 is within the preset range (ST9: NO), it is conceivable that the cause of failure is not the liquid feed tube 142 of the components forming the flow path but the detached cannula 113 included in the injector 11. In this case, the first controller 134 displays, on the monitor 204, that the cause of failure is present in the injector 11 including the cannula 113, to report the replacement to the user.

As described above, in the second embodiment, in the case in which the output during the reverse rotation of the motor 136 is within the preset range, the motor 136 again rotates in the rotation direction identical to that during the liquid feeding. Then, based on the output of the rotation detection unit 132 at that time, discrimination is performed between the replacement of the liquid-feeder disposable unit 14 and the replacement of the injector 11. Therefore, the cause of failure can be specified in more detail than in the first embodiment, and more detailed information can be reported to the user that only the failed component is replaced instead of the entire device.

Furthermore, the first controller 134 determines occurrence of blockage in any of the cannula 113 and the support member 114 or the liquid feed tube 142, with separation of the cannula 113 and the support member 114 from the liquid feed tube 142 verified through the mounting detection unit 139. As described above, the liquid feeder 12 including the liquid feed tube 142 has been separated from the injector 11 including the cannula 113 punctured into the living body. Thus, the medical liquid no longer enters or exits the living body when the cause of failure is identified, so that there can be prevented an effect on the living body.

Note that the present invention is not limited to only the above-described embodiments, and various alternations can be made within the scope of the claims. In the above description, there has been described the embodiments in which the failure is displayed on the monitor 204 when the failure of the driving system component such as the motor 136 or the like, or the component such as the liquid feed tube 142 can be identified. However, the present invention is not limited to the embodiments. In addition to the above, instead of displaying the cause of failure on the monitor 204, a pattern in frequency of an alarm, or a pattern of a melody and the like may be used to report to the user that the cause of failure is in the component such as the motor 136 or the component such as the liquid feed tube 142 or the like. Furthermore, in the above-described embodiments, the medical liquid administration device that administrates insulin has been described as an example; however, the present invention is not limited to insulin. As a medical liquid to be administrated, there may be used other various medical liquids such as analgesics, anticancer drugs, human immuno-deficiency virus (HIV) drugs, iron chelators, therapeutic agents for pulmonary hypertension, or the like.

This application is based upon and claims the benefit of priority from Japanese Patent Application No. 2016-188563, filed on Sep. 27, 2016, the disclosure of which is incorporated herein by reference in its entirety.

REFERENCE NUMERAL LIST

10 LIQUID-FEEDER MAIN BODY
11 INJECTOR
113 CANNULA (FLOWING PORTION, FIRST FLOWING PORTION)
114 SUPPORT MEMBER (FLOWING PORTION, FIRST FLOWING PORTION)
12 LIQUID FEEDER
13 LIQUID-FEEDER REUSABLE UNIT
14 LIQUID-FEEDER DISPOSABLE UNIT
100 INSULIN ADMINISTRATION DEVICE (MEDICAL LIQUID ADMINISTRATION DEVICE)
131 DRIVE MECHANISM
132 ROTATION DETECTION UNIT (DETECTION UNIT)
132a INTERCEPTING MEMBER
132b LIGHT EMITTING UNIT
132c LIGHT RECEIVING UNIT
134 CONTROL UNIT
134a FIRST CONTROLLER
136 MOTOR
138 MOTOR DRIVER
139 MOUNTING DETECTION UNIT (CONNECTION DETECTION UNIT)
141 MEDICAL LIQUID STORAGE
142 LIQUID FEED TUBE (FLOWING PORTION, SECOND FLOWING PORTION)
203 SECOND CONTROLLER
204 MONITOR (REPORTING UNIT)

What is claimed is:
1. A medical liquid administration device comprising:
a medical liquid storage storing a medical liquid;
a flow path comprising:
  a first flowing portion comprising a cannula configured to be punctured into a living body, and
  a second flowing portion separably connected to the first flowing portion, the second flowing portion comprising a liquid feed tube and configured to receive the medical liquid from the medical liquid storage and to provide the medical liquid to the first flowing portion;
a drive mechanism comprising a motor configured to generate a driving force for feeding the medical liquid stored in the medical liquid storage to the flow path;
a detection unit configured to detect an operating state of the drive mechanism; and
a controller configured to receive an output from the detection unit and to control the drive mechanism,
wherein the controller is programmed such that, when the output from the detection unit indicates that the operating state of the drive mechanism is outside a first preset range, the controller:
  (i) stops liquid feeding from the flow path,
  (ii) determines that a blockage in the flow path has occurred when, with the motor rotating in a reverse rotation direction relative to a rotation direction of the motor during the liquid feeding, the output from the detection unit indicates that the operating state of the drive mechanism is within the first preset range, and (iii) determines that a failure in the drive mechanism has occurred when, with the motor rotating in the reverse rotation direction relative to the rotation direction of the motor during the liquid feeding, the output from the detection unit indicates that the operating state of the drive mechanism is outside the first preset range, wherein the controller is programmed such that, when the controller determines that the second flowing portion has been separated from the first flowing portion and that the blockage in the flow path has occurred, the controller:

(i) causes the motor to rotate in a rotation direction identical to the rotation direction of the motor during the liquid feeding, (ii) determines that a blockage in the first flowing portion has occurred when the output from the detection unit, while the second flowing portion is separated from the first flowing portion, indicates that the operating state of the drive mechanism is within a second preset range, and (iii) determines that a blockage in the second flowing portion has occurred when the output from the detection unit indicates that the operating state of the drive mechanism is outside the second preset range.

2. The medical liquid administration device according to claim 1, wherein the controller is programmed such that the first preset range is different than the second preset range.

3. The medical liquid administration device according to claim 2, further comprising: a reporting unit configured to report the failure in the drive mechanism or the blockage in the flow path.

4. The medical liquid administration device according to claim 1, further comprising:

a connection detection unit configured to detect whether or not the first flowing portion and the second flowing portion are connected, wherein the controller is programmed to determine that the second flowing portion has been separated from the first flowing portion based on an output of the connection detection unit.

5. The medical liquid administration device according to claim 4, further comprising: a reporting unit configured to report the failure in the drive mechanism or the blockage in the flow path.

6. The medical liquid administration device according to claim 1, further comprising: a reporting unit configured to report the failure in the drive mechanism or the blockage in the flow path.

* * * * *